(12) United States Patent
Savvouras et al.

(10) Patent No.: US 11,266,442 B1
(45) Date of Patent: Mar. 8, 2022

(54) VISUALLY ASSISTED ENTRY OF A VERESS NEEDLE WITH A TAPERED VIDEOSCOPE FOR MICROLAPAROSCOPY

(71) Applicant: Enable, Inc., Redwood City, CA (US)

(72) Inventors: Odyssefs Ath. Savvouras, Athens (GR); Stephanos Papademetriou, Woodside, CA (US); Theofilos Kotseroglou, Hillsborough, CA (US); Ulrich R. Haug, Campbell, CA (US)

(73) Assignee: Enable, Inc., Redwood City, CA (US)

( * ) Notice: Subject to any disclaimer, the term of this patent is extended or adjusted under 35 U.S.C. 154(b) by 0 days.

(21) Appl. No.: 16/675,063

(22) Filed: Nov. 5, 2019

Related U.S. Application Data

(62) Division of application No. 14/935,325, filed on Nov. 6, 2015, now Pat. No. 10,463,399.

(Continued)

(51) Int. Cl.
| | | |
|---|---|---|
| *A61B 1/313* | (2006.01) | |
| *A61B 17/34* | (2006.01) | |
| *A61B 1/05* | (2006.01) | |
| *A61B 1/015* | (2006.01) | |
| *A61B 1/00* | (2006.01) | |

(Continued)

(52) U.S. Cl.
CPC ...... *A61B 17/3474* (2013.01); *A61B 1/00154* (2013.01); *A61B 1/015* (2013.01); *A61B 1/05* (2013.01); *A61B 1/00177* (2013.01); *A61B 17/3403* (2013.01); *A61B 17/3496* (2013.01); *A61B 90/361* (2016.02); *A61B 2017/00004* (2013.01); *A61B 2017/00473* (2013.01)

(58) Field of Classification Search
CPC ............ A61B 17/3474; A61B 17/3478; A61B 2017/348; A61B 17/3498; A61B 17/3421; A61B 17/3423; A61B 2017/3425; A61B 2017/3427; A61B 1/00154; A61B 1/015; A61B 1/04; A61B 1/05; A61B 1/267; A61B 1/2676; A61B 17/34; A61B 17/3476; A61B 90/361; A61B 2017/3445; A61B 2017/3447; A61B 1/313; A61B 1/3132
USPC ........ 600/109, 112, 114, 121–122, 127–130, 600/156, 158, 160
See application file for complete search history.

(56) References Cited

U.S. PATENT DOCUMENTS

| | | | |
|---|---|---|---|
| 6,387,043 B1 * | 5/2002 | Yoon ................. | A61B 1/00052 600/104 |
| 6,656,160 B1 * | 12/2003 | Taylor ............... | A61B 17/3496 604/158 |

(Continued)

FOREIGN PATENT DOCUMENTS

WO   WO-2014170338 A1 * 10/2014 ......... A61B 18/1487

*Primary Examiner* — Ryan N Henderson
*Assistant Examiner* — Pamela F Wu
(74) *Attorney, Agent, or Firm* — Thomas M. Freiburger

(57) ABSTRACT

A Veress needle is modified to receive a forward-looking miniature videoscope through the cannula of an insufflation tube of the Veress needle. The modified instrument enables direct viewing of progress of the instrument through tissue to the peritoneal cavity of a patient, for proper location of the needle and insufflation of the cavity via the needle. The videoscope has an elongated shaft of smaller diameter than the cannula of the insufflation tube for passage of insufflation gas with the scope in place. In another embodiment a needle is fitted with a miniature videoscope to provide the same function, with the needle's cannula serving as an insufflation tube.

4 Claims, 9 Drawing Sheets

Related U.S. Application Data

(60) Provisional application No. 62/076,417, filed on Nov. 6, 2014.

(51) Int. Cl.
*A61B 17/00* (2006.01)
*A61B 90/00* (2016.01)

(56) References Cited

U.S. PATENT DOCUMENTS

| | | | | |
|---|---|---|---|---|
| 2003/0158521 A1* | 8/2003 | Ameri | ............... | A61B 17/3403 604/117 |
| 2005/0288622 A1* | 12/2005 | Albrecht | ............ | A61B 17/3474 604/23 |
| 2007/0123840 A1* | 5/2007 | Cox | ................... | A61B 17/0057 604/514 |
| 2008/0033450 A1* | 2/2008 | Bayer | ................ | A61B 17/3417 606/108 |
| 2009/0043167 A1* | 2/2009 | Leiner | ................ | A61B 1/00119 600/156 |
| 2010/0262166 A1* | 10/2010 | Boraiah | ............. | A61B 17/0057 606/148 |
| 2010/0274081 A1* | 10/2010 | Okoniewski | ....... | A61B 17/3474 600/109 |
| 2011/0313255 A1* | 12/2011 | Stanley | ............. | A61B 17/3474 600/205 |
| 2012/0197078 A1* | 8/2012 | Stanley | .................... | A61B 1/05 600/109 |
| 2012/0310147 A1* | 12/2012 | Poll | .................... | A61B 17/3439 604/24 |
| 2014/0243599 A1* | 8/2014 | Farin | ...................... | A61B 17/34 600/114 |
| 2016/0081712 A1* | 3/2016 | Heniford | ............. | A61B 5/0066 600/424 |
| 2016/0143662 A1* | 5/2016 | Mulier | ............... | A61B 18/1492 606/49 |

* cited by examiner

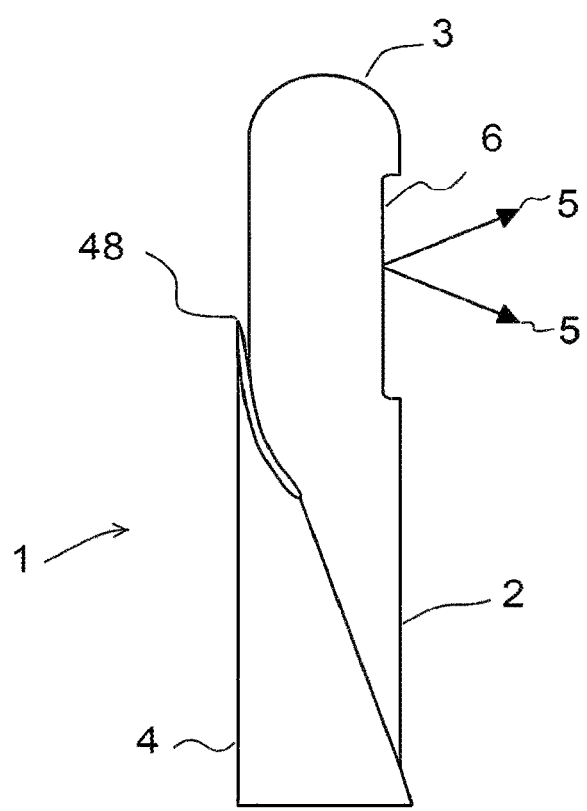
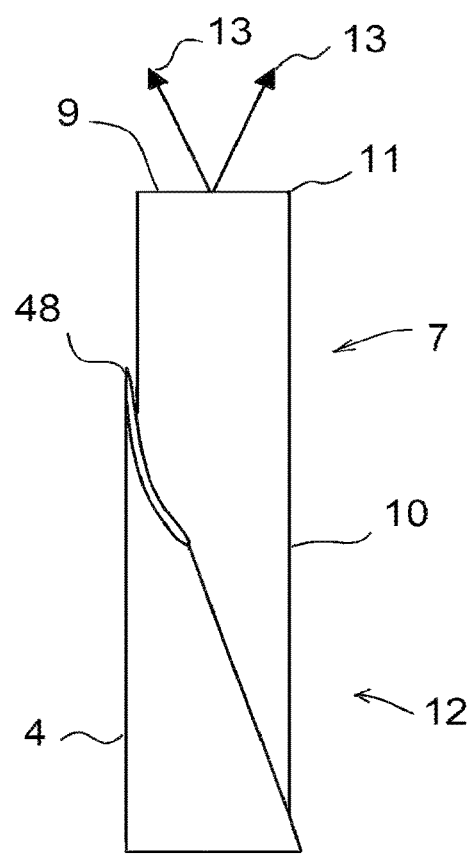
FIG. 1A
PRIOR ART
FIG. 1B

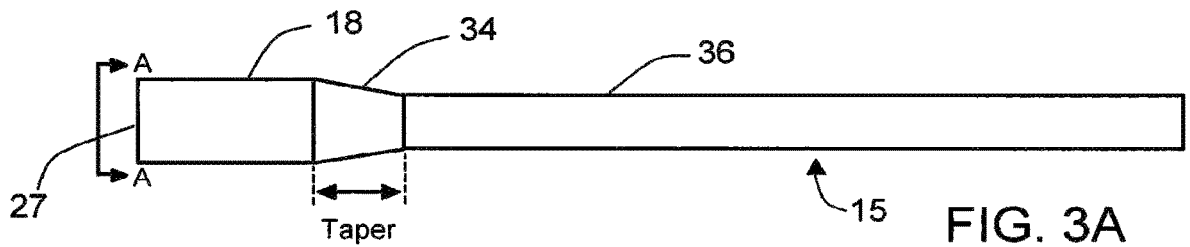
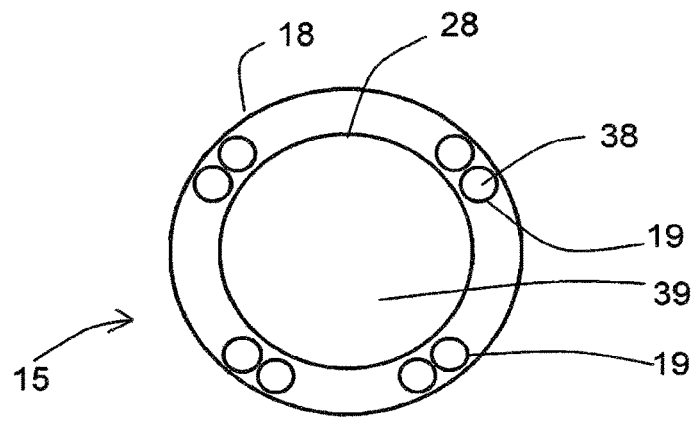
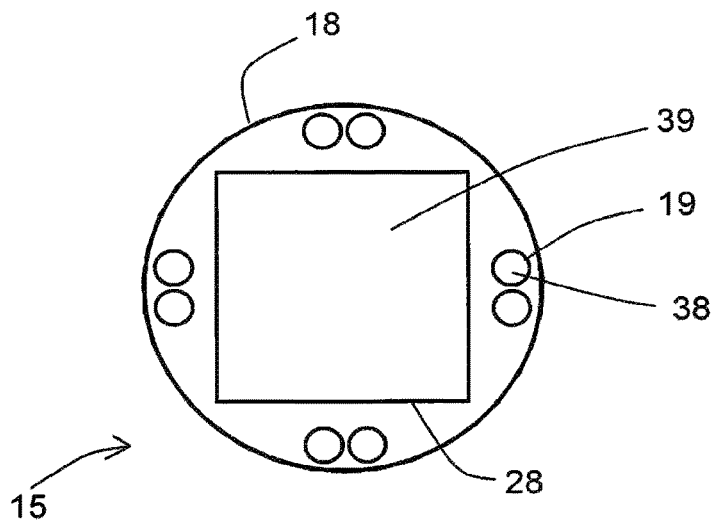

VISUALLY ASSISTED ENTRY OF A VERESS NEEDLE WITH A TAPERED VIDEOSCOPE FOR MICROLAPAROSCOPY

This application is a division of application Ser. No. 14/935,325, filed Nov. 6, 2015, now which claimed benefit of provisional application No. 62/076,417, filed Nov. 6, 2014.

BACKGROUND OF THE INVENTION

Laparoscopic, thoracoscopic, arthroscopic, and other endoscopic procedures are well-known surgical techniques that reduce patient recovery time due to minimal tissue damage. Generally, these surgical techniques rely upon the formation of one or more puncture wounds through which a body cavity, such as the peritoneal or the thoracic cavity, can be accessed. In laparoscopic surgery, once the peritoneal cavity has been entered, the same is insufflated with carbon dioxide gas, typically to a pressure of approximately 15 mm-20 mmHg, followed by the introduction of an endoscopic port with inserted trocar, which may either be bladed or blunt.

Most surgeons initially enter the peritoneal cavity using a Veress needle which is pushed blindly through the patient's fascia and peritoneum. The peritoneal cavity is then insufflated followed by the introduction of the laparoscopic port with inserted blunt or bladed trocar, which is also pushed blindly into the peritoneal cavity. Once positioned therein, the inner sheath of the trocar is removed and a laparoscope is introduced through the port to thus provide visualization within the cavity, see for example ("Comparison of direct insertion of disposable and standard reusable laparoscopic trocars and previous *Pneumoperitoneum with Veress needle*," Nezhat F. et. al. *Obstetrics & Gynecology* 78(1), (1991)).

The problem with such procedures, however, is the fact that the body cavity is entered blindly on two separate occasions: first, through the introduction of the Veress needle; and second, through the introduction of the laparoscopic port with inserted trocar, which can and on occasion does injure abdominal organs and major blood vessels.

To the extent laparoscopic surgery is performed upon a patient that has previously undergone an abdominal operation, the preferred surgical practice is to enter the peritoneal cavity under direct vision. In this regard, it is known that when a patient has undergone previous abdominal surgery, the abdominal contents can become adherent to the abdominal wall, making blind placement of a Veress needle and then blind placement of the port with inserted trocar a much more risky technique.

In light of such potential complications that can arise via entry into the peritoneal cavity during laparoscopic surgery, attempts have been made to provide means for safely entering into a body cavity utilizing direct visualization.

Notable Patents Describing Optical Trocars:

In light of such potential complications that can arise via entry into the peritoneal cavity during laparoscopic surgery, attempts have been made to provide means for safely entering into a body cavity utilizing direct visualization. Exemplary of such devices are those disclosed in U.S. Pat. No. 5,441,041, which utilizes a blade moveable between a non-deployed position and a deployed position to thus allow dissection under visualization of an endoscope.

A similar device attempting to provide direct visualization during entry into a body cavity is shown in U.S. Pat. No. 5,569,291. Such reference discloses a device for forming an entry into a body cavity performed under direct visualization of an endoscope. The dissecting portion of the device consists of a clear plastic conical tip with elevated dissecting blades that help advance it into the tissue via a twisting motion. The conical tip, however, is advanced bluntly into the tissue before the same can be identified and, as a consequence, incision of the tissue is performed without prior visualization. In fact, inadvertent entry into an organ cannot be avoided via use of such device, and it is only after the organ is entered, and hence damaged, that such matter can be appraised. Moreover, the use of clear plastic has substandard optical visualization due to optical properties inherent in such material, coupled with the conical shape, such that advancement of the tip fails to provide a clear visualization as the same is advanced through tissue.

Other devices that are similar in nature include U.S. Pat. Nos. 5,720,761; 5,551,947; 5,609,562; and 5,385,572, the teachings of all of which are expressly incorporated herein by reference.

A further related surgical instrument is disclosed in U.S. Pat. No. 6,007,481. Essentially, such device comprises an elongated sheath having a cone-shaped distal window. Such sheath has a screw-shaped blade to cut through tissue, while a scope can also be inserted to view the tissue penetration through the distal window. A second scope is proposed to also be able to get to the distal tip off the conical window for viewing distal to the point of the conical tip. This patent teaches the use of a fiberscope for visualization which implies a constant diameter scope with poor image quality due to the small number of pixels. More importantly viewing is limited by the inability of the viewing scope to get past the distal tip of the cutting sheath.

Furthermore all of the above mentioned prior art devices need a large incision and are taught to be used with a constant Outside Diameter (OD) viewing scope.

Commercial Optical Trocars:

Some commercially available laparoscopic entry systems with optical aid include the VersaStep (by Covidien Ltd.) with a trocar that can support a laparoscope going through a pre-inserted smaller but expandable needle. The first entry of the small needle is still blind, and the final wound made by the larger trocar still implies a larger trauma through the abdominal wall. Furthermore visualization is not possible during entry or insufflation.

The Visiport (by Covidien Ltd.) consists of a hollowed trocar with a wire blade that can cut through tissue, and a spherical crystal end. It can support a zero degree forward viewing laparoscope for inspection of entry through tissue.

The EndoTip trocarless visual cannula entry system by Karl Storz GmbH utilizes a spiral radial force version of the above mention optical large trocars that reduces the amount of axial force needed to get through the tissue while allowing for a laparoscope to monitor entry through the abdominal wall. But it is still a large device that requires an equally large incision, including a large and expensive laparoscope.

For the prior art described earlier as well as the commercial products introduced above, despite their ability to optically display tissue layers on the monitor during entry, these instruments retain either the conventional push through trocar and cannula insertion dynamics where entry is achieved by palming the entry device and applying considerable perpendicular axial pressure force (because of their very large diameter >5 mm-15 mm diameter cutting needles—or even larger), towards the abdominal cavity or radial force for the EndoTip, to propel the device into the peritoneum. Furthermore all these devices require a large incision of 10 mm-15 mm for the large trocar to get through the tissue and support large instrument entry. They penetrate tissue by tearing it, not puncturing it like a needle. Also the conventional visualization laparoscopes they use are constant in their outside diameter all along their length and large in diameter as well, >5 mm. Also the ones that require insufflation prior to their use, by design, are part of a second entry into the abdomen, and assume a prior blind entry has already been made.

Because of all of the above, such commercial devices would never be possible to accommodate outpatient, minimally invasive laparoscopies that may not require anesthesia. Not all of the above mentioned commercial products can accommodate pneumoperitoneum with the proposed laparoscope in place. The ones that can, have even larger diameter cutting cannula to leave enough annular space between the laparoscope OD and the inside diameter (ID) of the sheath it goes through. Their use depends on another puncture that has been made prior to their use for insufflation. Descriptive pictures and more details for such commercial instruments can also be found at laparoscopy.net/safe/safe3.htm.

Commercial Optical Veress Needle:

Better optics, miniaturization and advances in instrumentation allowed improvements in rigid and flexible narrow caliber micro-laparoscopes that require very small diameter entry ports with potential advantages. Some have introduced a visual entry system that requires a 1.2 mm semi-rigid zero degree micro-laparoscope that fits into a modified Veress type needle (Optical Veress Entry System; Karl Storz Endoscop GmbH, Tuttlingen, Germany). One major advantage of such system is that it may be inserted in the umbilicus or the left upper quadrant, and subsequent ancillary ports can be inserted under direct vision ("*Optical Veress as an entry technique.*" *Gynaecol Endosc*, 8:379-92, (1999)). This reusable system, like other optical entry instruments, is safest when applied after insufflation ("*Recent advances in endoscopic entry techniques,*" *Rev. Gynecological Practice*, 1, 60-69, (2001)). The system offers poor optics (being a fiberoptic scope). In addition, these expensive and very delicate instruments fracture easily given their narrow diameter and top-heavy camera end. They can be applied through the left upper quadrant in high-risk cases, during diagnostic conscious pain mapping and in critical care or outpatient diagnostic units ("*The role of microlaparoscopy in the diagnosis of peritoneal and visceral adhesions and in the prevention of bowel injury associated with blind trocar insertion,*" Audebert A J. *Fertil Steril;* 73:631-5, (2000)).

The poor quality of the optics in these mini laparoscopes, and their fragility (due to the coherent imaging fiber bundle construct; fiberscope) render them impractical to use. Furthermore no teachings are made of a tapered scope design that can accommodate a high-resolution digital sensor while it can still allow insufflation through a standard small Veress needle.

Also U.S. Pat. No. 4,869,717 describes a Veress needle that can accommodate an instrument. They propose a complicated Veress needle modification that can receive an instrument (including an imaging scope, although they do not directly mention that) by adding an outer sheath that is integrated to the outside of the needle shaft of a practically standard Veress needle. Once insertion and pneumoperitoneum is achieved the needle along with the inner insufflation port can be removed while the outer sheath can remain in place to be used to pass through other instruments. This requires an extended design change to a Veress needle, which in addition makes a larger puncture than the underline Veress needle that they modified (since the sheath that remains is exterior to the Veress needle). Much different than what we propose to do. In addition, from the architecture of their modality, insufflation must be initiated first and then one can insert an instrument. Furthermore they are no teachings in this patent about a tapered visualization scope.

There is thus a substantial need in the art for a system and method that can enable a surgeon to selectively enter a body cavity, vessel, or organ, for purposes of performing endoscopic procedures whereby the surgeon is provided with direct visualization during entry such that tissue separation can be visualized and organ and tissue damage can be avoided (i.e., the surgeon can see the tissue prior to dissecting the same), while at the same time, the instrument penetrating the tissue has a small overall OD (less than 3.1 mm and preferably less than 2.1 mm, like a small size standard Veress needle) that requires a small incision of less than 2 mm for its entry, and can support abdomen insufflation while at the same time provide images and live video of the area distal to the puncture instrument; and yet despite its small size, the visualization scope can produce high quality images. Finally because of the small diameter of the penetrating tool and necessary incision size, outpatient micro-laparoscopes can also be supported.

OBJECT OF THE INVENTION

Commercially available, miniature, digital camera sensors, with high number of imaging pixels that can be used to construct small OD videoscopes are available and are becoming smaller as time progresses (without losing resolution). A videoscope is an imaging device that utilizes a digital imaging sensor at its distal tip, including an imaging lens, and illumination is provided either via optical fiber transmission or by having LEDs at its distal tip as well. A micro-objective lens is also necessary to be positioned distal to the digital imaging sensor to image the space distal to it onto the active area of the sensor. If optical fibers are used for illumination they need to run along the length of the videoscope from its proximal end all the way to the distal end. If LED's are used for illumination, the OD of the distal tip of the videoscope is larger than when fibers are used for illumination, as the LEDs need to be packaged and heat-sinked appropriately for proper use. This action by default increases the overall cross-sectional space needed when LEDs are utilized for illumination in an imaging scope. The image is carried to the proximal end of the scope via electrical cables attached to the back end of the digital sensor for further processing and display.

It is the object of this invention to utilize modern miniature (smallest distal tip OD possible), high-resolution digital imaging sensor with fiber optic illumination to construct a novel videoscope. It is a further object of this invention to teach how the number and size of the optical fibers along with the size of the electrical cable can be chosen so that the overall OD of the fibers and electrical cable assembly (in a closed packed formation) can be smaller than the OD of the distal tip of the videoscope housing the digital sensor. Such variability in the OD of the distal versus the proximal end of the proposed videoscope construct results in a tapered design; an essential element of the design of the videoscope taught in this patent application.

It is the essence of the taper design of the proposed videoscope which makes the following possible simultaneously:

For a given miniature digital imaging sensor the tapered design will allow the maximum number of pixel sensor (highest resolution available) to be used to construct a small-enough tip videoscope that can fit down the smallest possible gas-insufflation sheath of a standard Veress needle, while providing a large enough annular space between the tapered-down shaft of the scope and insufflation sheath of the needle for simultaneous gas insufflation. Thus, allowing for normal gas insufflation through the Veress needle without causing pressure alarms while the visualization scope resides inside the Veress needle, and while keeping the overall size of the Veress needle as small as possible and preferably the same as any standard size miniature Veress needle.

Another object of this invention is to show how a standard Veress needle can be modified so that it can be used along with the proposed tapered videoscope. It is also the object of this invention to show how such tapered, miniature, high-resolution videoscope can be used as a stylet (the visualization stylet) and inserted through the modified Veress needle to visually assist the entry of the Veress needle through tissue, during puncture of the tissue, as well as insufflation, and beyond without having to be removed; thus greatly increasing the safety of the puncture as well as the procedure that follows after the primary puncture, since the body cavity reached can be under constant direct visualization throughout.

Finally another object of this invention is to use such combination of instruments for regular laparoscopic surgeries or diagnostic procedures. The small incision and tissue trauma due to the miniature OD of the Veress needle proposed here translates to less pain for the patient, faster recovery times, and less expensive procedures compared to regular laparoscopic procedures or regular surgery.

SUMMARY OF THE INVENTION

The current invention describes the design of a novel videoscope with fiber illumination (visualization stylet) to be used through any standard existing size Veress needle and assist in the direct visualization of the passage of the Veress needle through tissue, during insufflation, and post insufflation during the whole length of the laparoscopic procedure. Such a tool can address the problems that have been identified in the literature with the first blind puncture of a Veress needle to achieve pneumoperitoneum during laparoscopic surgery, and worse yet with the more dangerous second (initially blind) puncture of the much larger trocar for insertion of a large-size laparoscope and illumination into the abdomen after insufflation of the abdominal cavity (see for example "*Entry complications in laparoscopic Surgery*" *J. Gynecol Endosc. Surg.* 1(1): 4-11, 2009). Furthermore, since the proposed visualization stylet can remain in place without impeding the function of the Veress needle, it can also be used as a quick and efficient diagnostic laparoscopic tool that requires only one small puncture through the abdomen. The utility of microlaparoscopy (one that could be performed in an outpatient setting, possibly under local anesthesia) has been identified since the 1990s (see for exampleobgyn.net/laparoscopy/microlaparoscopy and "*Microlaparoscopy using an optical Veress needle inserted at Palmer's point*," *Gynecological Endoscopy* 8, 115-116 (1999)).

Innovative, high resolution, miniature, complete (including illumination) videoscopes will bring microlaparoscopy to the forefront. Methods of using such miniature digital imaging tools to construct a visualization stylet to be used during laparoscopic procedures are also disclosed.

As the field of miniature digital imaging cameras and novel illumination schemes for such miniature architectures is progressing, we are at a point where a small diameter (even <1.4 mm OD) complete videoscopes can be constructed without having to sacrifice significantly the image resolution it can produce. Approximately 1 mm square chips (or slightly less) packages with digital imaging sensors that carry tens of thousands of pixels are already commercially available: see for example Awaiba's naneye CMOS sensor awaiba.com/product/naneye-family-overview/with 62,500 pixels). Or the MiniCam CCD camera by Medigus Ltd. (Omer, Israel) with 50,000 pixels ("*Miniature camera for enhanced visualization for single-port surgery and notes*", *Journal of Laparoendoscopic & Advanced Surgical Techniques*, 22, (10):984-8, (2012)). Or better yet the high-resolution finished complete videoscope tip (imaging sensor and illumination with less than 1.4 mm OD; thus from FIG. 4A, $G_{id} <= 1.4$ mm) that Enable Inc. (Redwood City Calif., USA) will be introducing with 160,000 pixels. Such digital imaging cameras and finished videoscope tip products are necessary in constructing the aforementioned visualization stylet with a cross sectional diameter smaller than the current standard ID of the inner gas-flow sheath of a standard Veress needle.

DESCRIPTION OF THE DRAWINGS

FIG. 1A shows the tip of a spring-action blunt inner cannula that carries insufflation gas, with the outer cannula or needle indicated with a sharp, angled tip, and also showing gas flow, representative of a prior art standard Veress needle.

FIG. 1B shows a modified Veress needle inner cannula tip according to the invention, indicating modified direction of gas flow, to accommodate a visualization stylet of the invention to be placed in the inner cannula.

FIGS. 3A, 3B and 3C show different regions of the distal stiff segment of the visualization stylet of the invention. FIG. 3B shows an end view of the stylet of FIG. 3A, and FIG. 3C is similar to FIG. 3B but showing a modified embodiment with a square lens or window.

In FIG. 4A the stylet distal tip is pushed out, distal to the gas-flow sheath, showing an annular clearance for gas flow; in FIG. 4B the stylet distal tip has not yet cleared the distal end of the gas-flow sheath.

FIG. 10B shows the cap as pushed off and away by the emergence of the visualization stylet from the sheath.

DETAILED DESCRIPTION AND PREFERRED EMBODIMENTS OF THE INVENTION

Figure 2:
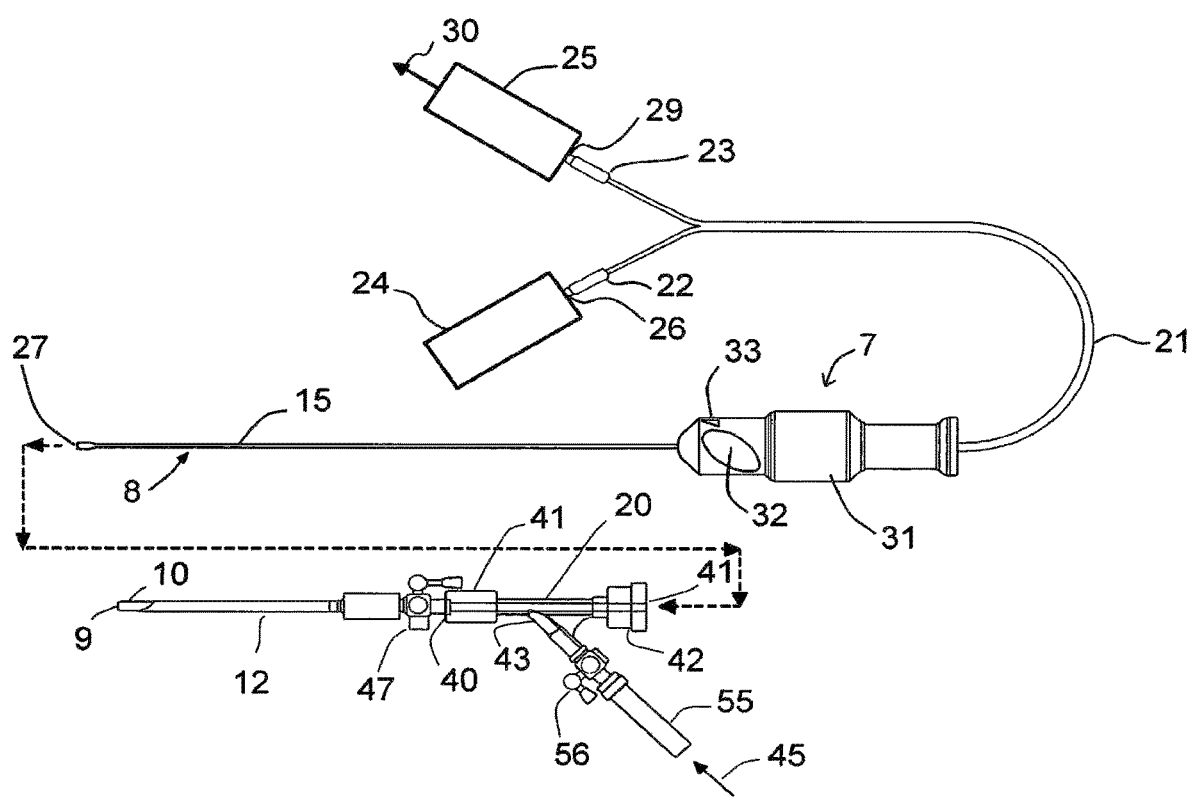
FIG. 2 is an exploded view indicating a visualization stylet of the invention, and insertion of the stylet through a modified Veress needle as in FIG. 1B. The dashed line indicates insertion of the distal end of the stylet through the proximal end of a hemostasis valve Y-connector of the Veress needle.

A. Preferred Changes to a Standard Veress Needle:

Minimal changes can be made to a standard Veress needle 1 to accommodate the functionality of this embodiment of the proposed visualization stylet. Typically the movable inner sheath 2 of the Veress needle (the spring-action blunt inner-cannula that carries the insufflation gas) has a rounded distal tip 3 with a side port 6 for the insufflation gas 5 to pass through, as shown in FIG. 1A. This longitudinal sheath 2 will also be referred to as the gas-flow sheath. The rounded distal tip 3 of this sheath helps prevent any inadvertent damage during the first abrupt puncture of the abdominal cavity with the needle 4 portion of the Veress needle, while allowing for the passage of gas 5 from the side port 6 (after puncture through the abdomen). The passage and direction of gas flow through the side port 6 is indicated by the arrows 5 in FIG. 1A; standard use of a Veress needle insufflation.

The current embodiment of the visualization stylet 7 consists of a forward looking videoscope 8 (viewing along the axis of the shaft of the stylet). See FIG. 1B. Thus, in a modification the rounded tip 3 of the gas-flowing sheath of a standard Veress needle can be cut off, preferably at the proximal end of the side gas flow window 6, for the stylet 7 to be able to see past as well as be pushed distal to the distal end 9 of the modified gas-flow sheath 10, FIG. 1B. Further processing of the distal edge 11 of the cut should be performed to bevel or round-off the edges of the distal opening 9 and present the body with as atraumatic an edge as possible. In this embodiment of the modified Veress needle 12, the insufflation gas goes out through the distal output port 9 of the movable gas flow sheath 10. The passage and direction of gas flow through the distal end 9 is indicated by arrows 13 in FIG. 1B.

Utilizing the commercially available Awaiba naneye2C camera awaiba.com/product/naneye/ and multimode illumination fibers, a visualization stylet and a modified Veress needle with the following dimensions were successfully constructed (TABLE 1).

TABLE 1

Figure 4A:
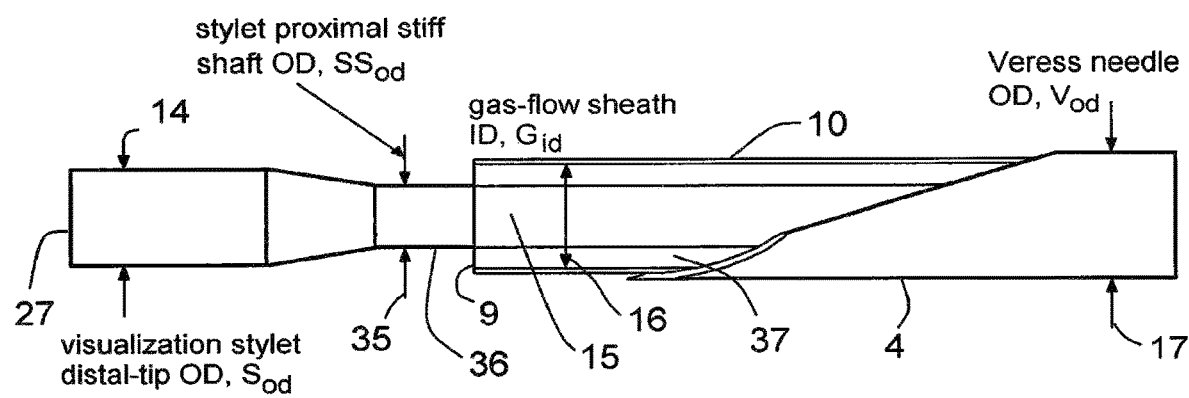
FIGS. 4A and 4B are side views, showing relative sizes of different regions of the distal stiff segment of the visualization stylet with respect to the inside diameter of the gas-flowing sheath or cannula of the Veress needle.

See FIG. 4A. Critical dimensions of a preferred embodiment of the proposed device. Note $V_{od}$ 17 of the modified Veress needle 12 is the same as the OD of a standard small Veress needle 1. The table headers are explained in FIG. 4A.

| 17, $V_{od}$ | 16, $G_{id}$ | 14, $S_{od}$ | 35, $SS_{od}$ |
|---|---|---|---|
| 2.1 mm | 1.7 mm | 1.6 mm | 0.8 |

Preferably no modifications to the size (outside diameter $V_{od}$ 17) of a standard existing Veress needle are necessary, so long as the largest OD 14 of the stiff portion 15 of the visualization stylet 7 (14, $S_{od}$ as defined in FIG. 4A; its distal tip 18) is made smaller than the ID 16 of the inner insufflation shaft 10 of the Veress needle (16, $G_{id}$ as defined in FIG. 4A). In other words: $S_{od}<G_{id}$. Note that these dimensional relations are also defined in more detail later on. It is also preferred that $V_{od}$ 17 (the outside diameter of the Veress needle) is kept at under 2.1 mm (standard Veress needle OD, such as Karl Storz model number 26120JL (13 cm long). Other Karl Storz model number Veress needles (or similar models from other manufacturers) such as 26120J (10 cm long) and 26120JLL and 26120XL which are 15 cm and 18 cm long respectively can also be used and modified accordingly.

Importantly, no modifications to the functionality of the Veress needle are needed in order to use the proposed visualization stylet 7. The proposed visualization stylet 7 is a novel videoscope 8 construct with fiber illumination 19 (FIGS. 3B, 3C) that can easily be moved through the Veress needle 12 (even during insufflation) while continually viewing of the areas distal to the tip of the Veress needle. Note that the area of the distal end of the visualization stylet is about 2.0 mm².

Thus the visualization stylet 7 can provide images and live video during tissue penetration, during insufflation and post insufflation. Actually the design can allow for the visualization stylet to remain in place through the Veress needle (as shown FIG. 4A and FIG. 6) throughout the laparoscopic procedure without affecting the functionality of a typical standard diameter Veress needle or generating any pressure alarms from the gas insufflating pump.

Such a system can then be used for laparoscopic surgery that will be less painful both than regular laparoscopic procedures (that use larger incisions and diameter instruments) and obviously than regular surgery, while at the same time offer good quality images (due to the high-resolution miniature digital imaging sensors). Smaller and fewer incision also translate to faster recovery time for the patient, as well as lower cost procedures in general.

B. Preferred Embodiments and Description of the Visualization Stylet:

FIG. 2 is an exploded view indicating a visualization stylet of the invention, and insertion of the stylet through a modified Veress needle as in FIG. 1B. The dashed line indicates insertion of the distal end of the stylet through the proximal end of a hemostasis valve Y-connector of the Veress needle.

The device 7 will be referred to from here on as the visualization stylet or simply as the stylet.

The visualization stylet (FIG. 2) consists of 3 different functional elements along its length:

(1) A distal stiff segment 15, that gets inserted through the Veress needle 12. This is the portion of the visualization stylet that goes in and out of the Veress needle. It is longer than the length of the Veress needle and any other elements attached proximal to it (like the hemostasis valve Y-connector 20 described later on, and as shown in FIG. 2) so that its distal tip can comfortably be pushed past the distal end of the Veress needle when the distal tip of the handle touches the proximal end of the Y-hub, FIG. 6.

(2) A proximal flexible segment 21, that contains the proximal length of the illumination fibers and electrical conductors from and to the distal digital sensor. The proximal end of the flexible portion of the visualization stylet terminates in two connectors: an optical 22 and electrical 23 connector (FIG. 2) to be inserted into a light source 24 and image processing hardware 25 respectively. The optical connector 22 has all the illumination fibers 19 bundled closely together (close-packing) and polished at their proximal end. The electrical connector 23 has the proximal ends of all the electrical conductors necessary to carry signals to and from the digital imaging sensor. The number of conductors in the electrical cable assembly depends on the kind of digital sensor used. The manufacturer of the digital sensor dictates those specifications. The light source 24 has an appropriate receptacle 26 to receive the optical connector 22 of the flexible proximal segment 21 of the stylet 7 and appropriately designed coupling optics and light source to couple adequate light into the illumination fibers 19 for transmission all the way to the distal end 27 of the stylet 7 for proper imaging. Those knowledgeable in the art of optics and illumination can understand how the light source, coupling optics into illumination fibers 19, fiber transmission, number of fibers, size of fibers, and fiber numerical aperture are some of the important elements of the design to ensure proper amount of lighting of the distal viewing field of view. The F-number of the imaging micro-objective 28 in front of the digital sensor (camera) as well as the pixel sensitivity of the digital imaging sensor are also important factors that will dictate how well illuminated the field of view will appear. Reference to a camera or digital imaging sensor or camera herein is understood as including the imaging lens. Similarly the image processing hardware 25 has an appropriate electrical receptacle 29 to receive the electrical connector 23. This hardware/firmware translates the electrical signals from the digital sensor to an image to be displayed in a computer or onto a monitor, or a hand-held tablet or smart phone, or to a storage device (all such display and storage devices are indicated by arrow 30 in FIG. 2). The image processing hardware 25 can also have a display and removable storage to display and store images and video (hand-held design). Those knowledgeable in the art of digital imaging can understand how to put together such processing hardware.

Figure 6:
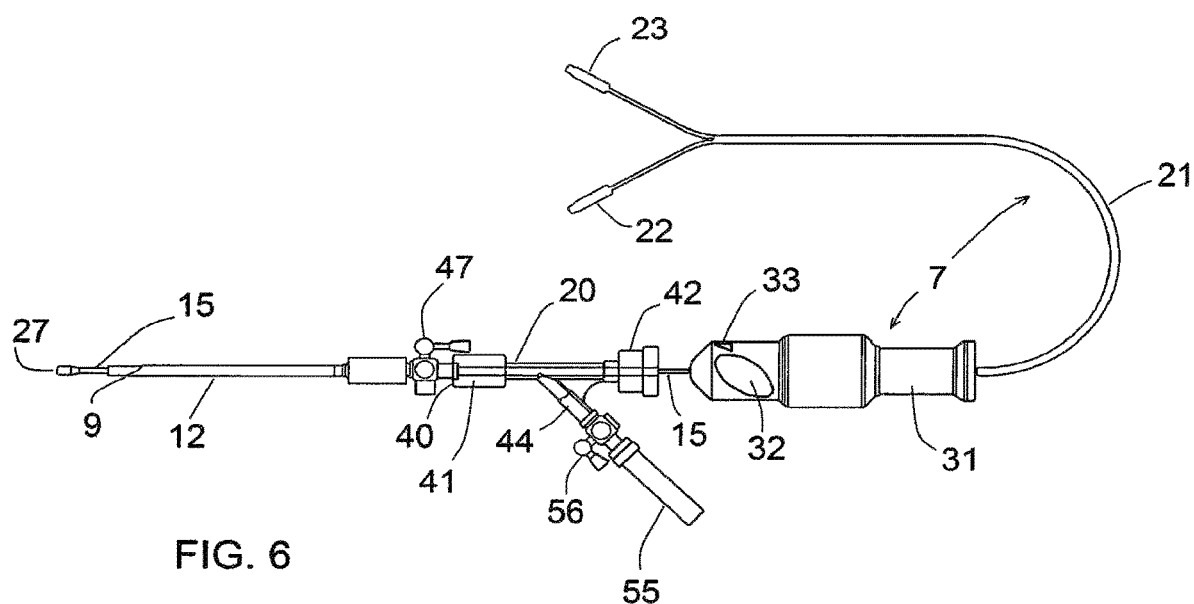
FIG. 6 is another view of the visualization stylet and Veress needle as inserted into and through the hemostatic Y-connector.

(3) Finally a handle or hub 31 is used that resides between the two aforementioned sections. The handle is larger in diameter than any of the ports of the Veress needle 12 or hemostasis Y-connector 20. The handle 31 should be designed so as to fit in the surgeon's hands comfortably for easy manipulation of the visualization stylet 7 (in-out through Veress needle, and tip-tilt manipulation of Veress needle with visualization stylet inserted in it). The proper asymmetries 32 can be designed in the handle 31 so that there is a preferred orientation that a surgeon will always hold onto that feels more natural to hold it than others. This way even without looking the surgeon holds the handle exactly the same way (by rotating in his/her hand until it feels natural). The handle 31 also serves as the part that limits how far past the Veress needle distal tip 9 one can push the visualization stylet distal tip 18 (FIG. 6). Since different length Veress needles are made to accommodate different size patients, different models of the visualization stylets can be made to match the length of any existing Veress needle model (along with other attachments like 20).

The handle 31 should also have a feature 33 on it that is both visible as well as protrudes so it can be felt by touch by the surgeon (without having to look at the handle). This feature 31 is shown in FIG. 2 as an arrow pointing down the distal end of the stylet 7, but it can have other shapes as well. It is also preferred that this feature is located in a place around the circumference of the handle so that when the surgeon feels the handle (even blindly by feeling asymmetry 32) the feature 33 becomes right side up as the ergonomics of the handle ensure a natural fit into the human hand.

During assembly of the stylet 7, the handle 31 is rotated appropriately and is attached to the stiff portion 15 of the stylet so that the images displayed on the monitor are right side up when the handle feature (arrow 33) is facing up. Clearly, any other pre-determined convention can be used during assembly so that when the doctor is seeing the feature (arrow 33) in a specific orientation it implies that the image is in some pre-determined orientation as well.

C. Further Description of the Stiff Distal Segment of the Visualization Stylet:

The distal stiff portion of the visualization stylet has three different regions: Two different diameter and length segments and a taper transition 34 between them (FIG. 3A).

(1) A distal short-length enlarged-diameter tip 18; which houses the digital imaging sensor chip and distal end of the illumination fibers 19.

Figure 4B:
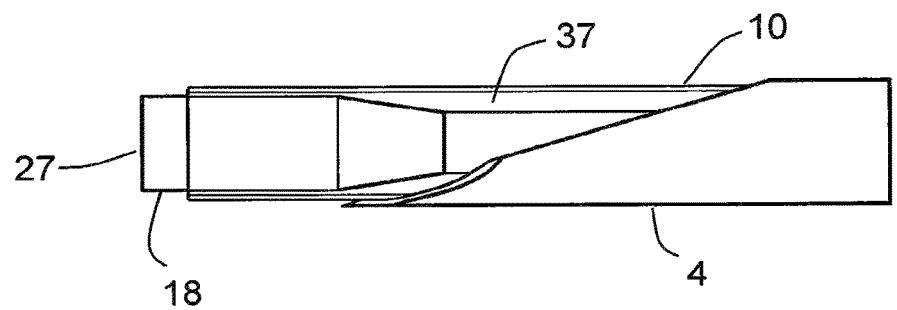

The digital sensor can be a CMOS or ccd type digital image sensor. From the miniature high-resolution digital imaging constructs described earlier, the imaging sensor (sometimes called the camera, or the digital camera chip) is the largest element. The critical dimensions of the visualization stylet 7 and modified Veress needle 12 are also defined in FIG. 4A. The diameter of the tip, 14 $S_{od}$, is dictated predominantly by the size of the digital imaging sensor, and then by the diameter of the fibers 19 used for illumination. The distal tip 18 is the largest OD portion of the visualization stylet 7 and can block (or greatly reduce) passage of the insufflation gas when it has not cleared the distal end 9 of the gas-flow sheath 10 of the Veress needle 12, FIG. 4B. This is a preferred feature of the stylet as this geometrical limitation can quickly offer feedback to the doctor as to the location of the distal tip of the stylet with respect to the opening of the gas flow sheath of the modified Veress needle, as a pressure alarm will quickly be generated if the gas flow is high enough and the system is in a configuration as depicted in FIG. 4B. The OD 14 of the distal tip 18, 14 $S_{od}$, is made so that it is slightly smaller than the ID 16 $G_{id}$, of the gas-flow sheath 10 of the Veress needle 12 so that it can still comfortably be passed through it (FIG. 4A and FIG. 4B). Thus it is necessary the following is satisfied for this embodiment:

$$S_{od} < G_{id}. \qquad \text{Equation 1}$$

For this embodiment of the device it is also necessary that: $SS_{od} < G_{id}$ (Equation 2) by enough margin so that no pressure alarms are generated by he insufflation pump when the gas is flowing at 15 L/min or preferably as much as 35 L/min.

$SS_{od}$ (see for example FIG. 4A) is the outside diameter 35 of the proximal 36 longer length and smaller diameter than distal tip 18 portion of the stiff distal segment 15 of the visualization stylet 7.

Note, to be more specific, Equation 2 defines the existence of an annular space 37 between the proximal shaft 36 of the stylet 7 and the ID 16 of the gas-flowing shaft 10, as indicated in FIG. 4. Such annular space 37, according to this embodiment, must be large enough to allow at least 15 L/min flow of $CO_2$ gas or preferably as much as 35 L/min (when the distal tip 18 of the stylette 7 completely clears the distal tip 9 of the gas-flowing sheath 10 of the Veress needle 12) with no pressure alarms. The needed clearance is discussed below in connection with FIG. 6A, another embodiment.

Those knowledgeable in the art of endoscopy and micro-imaging can understand how the distal end of a videoscope is constructed along with imaging micro-objective 28 and illumination fibers 19. It is preferred for the distal end 38 of the illumination fibers 19 to be flush with the distal surface 39 of the imaging lens 28 system that resides in front of the digital sensor (typical videoscope design). The distal surface 39 of the lens can be designed to be preferably flat allowing for the illumination-fiber distal surface 38 and lens distal surface 39 to be flat-polished together, FIG. 3B. Although FIG. 3B depicts a cylindrical lens, the micro-objective lens 28 can also be made to have a rectangular or preferably square outside shape (see FIG. 3C). This way it matches better the square typical cross sectional profile of the underlying imaging camera. The fibers 19 can then be arranged in a circular arrangement around the square profile of the lens, FIG. 3C.

The number of fibers 19 used and their size is a function of how large the OD 14 of the distal end of this enlarged distal tip 18 of the visualization stylet 7 can be (but must always satisfy Equation 1). Preferably, the size and number of the illumination fibers 19 must be such that when placed against the imaging lens 28 and camera chip sensor (FIG. 3B; where 8 fibers are shown as an example) they do not enlarge the cross sectional area of the distal tip of the stylet past the diameter dictated by the digital camera chip (defined by the diagonal of the rectangular digital sensor), or enlarge it enough but still satisfy Equation 1. Also note that Equation 2 must be satisfied at the same time as Equation 1. Thus the choice of the size of the fibers must be considered along with the size of the electrical connector so that Equation 2 can also be satisfied.

(2) A proximal longer-length and smaller-diameter 35 metallic shaft 36; it houses the proximal length of the illumination fibers and electrical wires from the digital sensor.

The OD 35 of this portion of the visualization stylet 7, 35 $SS_{od}$, is dictated predominantly by the size and number of illumination fibers and OD of the electrical conductor assembly attached to the digital imaging sensor and must be designed to satisfy Equation 2. This segment constitutes the shaft of the stylet 7 which is preferably made out of stainless steel, FIG. 3A. The reduced diameter 35 of the visualization stylet 7 is such that when the enlarged tip 18 is pushed out of the gas-flow sheath 10 of the Veress needle 12 the insufflation gas can easily flow through the needle without causing any pressure alarms from the gas pump, EQUATION 2 and FIG. 4A.

(3) Finally the tapered transition 34; It is the third characteristic geometrical feature of the stiff portion 15 of the visualization stylet 7.

It is the region residing between the two aforementioned fixed diameter lengths, FIG. 3A. This tapered segment 34 can preferably be made as a stainless steel insert whose proximal and distal diameters match well with the diameters of the perspective segments it mates with so that the outside surface of the stiff portion 15 of the stylet 7 is smooth with no sharp edges all along its length and along the tapered transition 34. The length of the tapered transition 34, $Taper_L$; as defined in FIG. 3A, should be kept as short as possible, and preferably less than 10 tip diameters 14:

$$Taper_L < 10 * S_{od} \qquad \text{Equation 3}$$

Tapered segment 34 can also be made as a flared out tapered segment of the long-length smaller diameter segment of the stiff portion of the stylet. Reinforcing the tapered transition area 34 with a metallic insert also prevents scraping material off of the stylet as the modified flat distal outlet edge of the gas-flow sheath 10 of the Veress needle 12, FIG. 1B, runs against the outside surface of the stylet especially as it is pulled back (FIG. 4B) into the gas-flow chamber 10 after it got pushed out (FIG. 4A).

It should be understood that although the taper 34 is preferred, the transition from small to larger diameter could be more abrupt if desired; a sharp ledge will function acceptably when the enlarged end is pushed out sufficiently. Simple curving transitions could be included at the distal end of the narrower section 36 and at the proximal end of the larger section 18.

D. Description of attachments to modified Veress needle:

In order to have the stylet 7 run through the proximal luer-lock input 40 of the modified Veress needle 12, a seal must be made to prevent gas leaking from this port. We achieve this by using a hemostasis Y-connector 20, FIG. 2. More specifically by connecting the rotating male luer lock 41 of a hemostasis Y-connector 20 (that may be also referred to as the Y-hub, 20) to the proximal luer lock port 40 of the Veress needle 12, FIG. 5. Sealing of the gas-flowing chamber can be performed on the proximal end 41 of the Y-hub 20 by tightening the hemostasis valve 42 against the proximal metallic sheath 36 of the visualization stylet 7. This way gas sealing is happening PROXIMAL to the gas-inflow shaft 10 of the Veress needle 12, FIG. 2. A commercially available Y-hub 20 such as QOSINA PN 80348, Hemostasis Valve 42 Y Connector with Rotating Male Luer Lock 41 and Female Luer Lock 43 sideport 44 can be used. Other similar products can perform the same function, such as QOSINA PN 33057, One Handed Hemostasis Valve Y Connector, Rotating Male Luer Lock/Female Luer Lock Sideport. A custom made Y-hub 20 that utilizes the same functionality and has the same mating connections on its three ports as the aforementioned QOSINA parts could also be used for this embodiment. But the commercially available parts are inexpensive, disposable, and have been extensively tested for their functionality.

Figure 5:
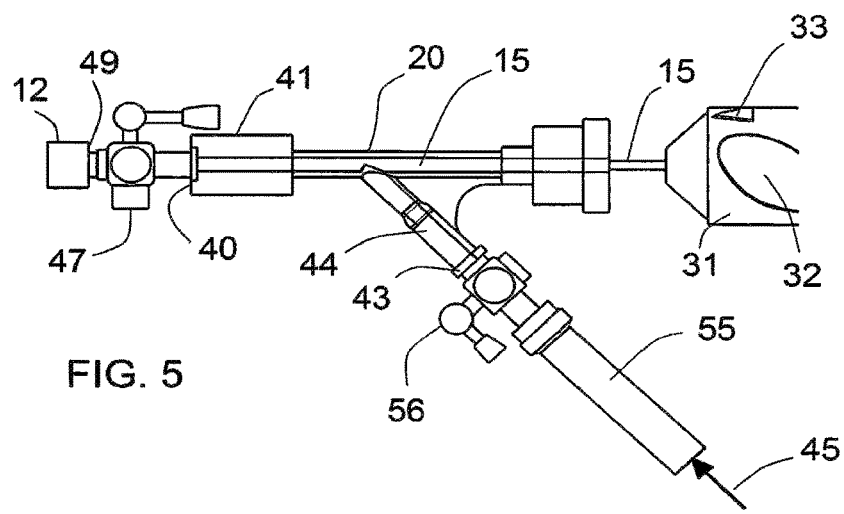
FIG. 5 is a detail view of the hemostatic Y-connector of the Veress needle and its attachment to the proximal end of the Veress needle of the invention.

These Y-hubs 20 are designed so that what goes through the center lumen can still be moved in and out (depending on how hard the hemostasis valve 42 is tightened), while significant sealing of whatever is flowing from the side port 44 (gas or liquid) can still be maintained (FIG. 5). Flow through the side port 44 is indicated by arrow 45 in FIG. 2 and FIG. 5). If the screw 42 of the hemostasis valve of the Y-hub 20 is turned tight, then the location of the visualization stylet 7 can be completely locked with respect to the Veress needle 12 as well, while providing for perfect gas seal. The other proximal port of the Y-hub (side port 44), presents with a female luer lock 43 so that the user can connect the tubing 55 from the insufflation gas pump through a valve port 56 (FIG. 5). Other mating connection sex adapters can also be utilized for as long as the parts can mate correctly to the ports of the Y-hub 20. The seal of the hemostatic valve 42 of a Y-hub 20 (whether partially tighten or completely tighten) can allow for long-term visual inspections of the insufflated abdomen through the visualization stylet 7 without significant (or any) loss of gas pressure from the abdomen, as the gas pump can easily be continually flowing gas through the system around the small diameter stiff portion 36 of the distal shaft 15 of the stylet 7 (annular space 37 between $G_{id}$ and $SS_{od}$ in FIG. 4A and TABLE 1) even at high flow rates with no pressure alarms while maintaining constant pressure in the abdomen and make up for any gas loss through the system.

Finally, since the functionality of the Veress needle native insufflation stopcock 47 has been disabled (needs to remain open at all times so that visualization stylet 7 can be freely passed through it), it can easily be replaced with a (preferably disposable) inline flow control switch 56 such as QOSINA PN 97337. This is shown in FIG. 2 and FIG. 5 preferably attached to the side port 44 of the Y-hub 20 and can control the gas flow from the insufflation pump (not shown in any figures).

Description of Preferred Use of the Hardware:

See FIG. 6 for preferred final placement of stylet 7 with respect to modified Veress needle 12.

(a) Inserting the visualization stylet through the slightly modified Veress needle: After the spring-action blunt inner cannula 10 that carries the insufflation gas through the Veress needle 12 has been modified as described in FIG. 1B, the visualization stylet 7 can be passed through it to provide live viewing of the passage of the Veress needle tip 48 through tissue and eventually distal to it once the needle penetrates through the abdominal wall. The original Veress needle insufflation stopcock 47 is kept open at all times (no use for it since the visualization stylet is going through the gas-flow sheath 10). The function of this valve can easily be replaced by the addition of a disposable and removable inline flow-control switch 56 attached on the Y-hub 20 side-port 44; discussed earlier, as shown in FIG. 2.

(b) During tissue penetration, the distal end 27 of visualization stylet 7 is kept inside the gas-flow sheath 10 and near its distal end 9 to monitor penetration through tissue and passage through peritoneum. Keeping the distal end 27 of visualization stylet a little proximal to the distal end 9 of the gas flow sheath 10 during insertion will also prevent excessive contamination of the distal optic 28 from tissue debris and blood during penetration.

(c) Once the Veress needle 12 goes through the abdominal wall and peritoneum, the visualization stylet 7 is pushed so that its larger OD 14 distal tip 18 can completely clear the distal end 9 of the gas-flow sheath 10, FIG. 4A; i.e. pushed distal to it. The in-line flow-control switch 56 attached to the Y-hub 20 is opened and insufflation can commence. Gas flow can also be manually controlled by the user by slightly inserting the large OD tip 18 of the visualization stylette 7 back into the gas-flow sheath 10, FIG. 4B. Once the enlarged distal tip 18 of visualization stylet 7 clears the distal end 9 of the gas-flowing sheath 10, FIG. 4A, the smaller diameter 35 of the stylet 7 allows for normal flow of gas into the abdomen for insufflation WHILE visualizing stylet 7 is within the penetrating instrument.

(d) The ergonomics of the handle 31 and the dial 33 on it assist the doctor in having an understanding of orientation and in proceeding with the visualization of abdomen.

Once the peritoneal cavity is inflated the surgeon can view the interior of the cavity to select a site (or several) for additional port(s) for trocars, e.g. side ports. A site can be selected and the needle tip and scope can be aimed to direct a light beam at the site from inside, visible through the tissue and skin, and the spot can be marked on the skin. The needle is then removed and used to penetrate that site to provide another port (lateral port). A large main trocar (e.g. 10 mm) is inserted in the first, main port, with visual monitoring from inside, using the videoscope in the needle, so that the large trocar is inserted properly and safely. Additional, usually smaller trocars are then inserted as needed.

At the termination of the surgical procedure, the surgeon can better close the ports using the invention. With the needle/scope in one of the smaller ports, the large trocar can be viewed from inside, and when removed, the closure can be performed using RF energy (RF instrument inserted through main port), this procedure being observed on the video screen. In conventional procedures the large central port typically could not be closed in this way, but only stitched from outside. If a total of three ports have been formed, one of the small ports can first be closed, under visualization through the scope (or via a larger scope through the main port), and using RF energy applied in the small port. Then the large trocar can be sealed in the same way, under observation inside the cavity using the needle/scope of the invention through the third, remaining port. The third port must be closed externally, but it is a small port and this can easily be done.

OTHER EMBODIMENTS OF THE INVENTION

In another embodiment of the stylet 7 and modified Veress needle 12 along with the disclosed tools of FIG. 2 and preferred modality of use, can be applied to any method that can enable a surgeon to selectively enter a body cavity or organ, for purposes of performing endoscopic procedures whereby the surgeon is provided with direct visualization during entry such that tissue separation can be visualized and organ and tissue damage can be avoided (i.e., the surgeon can see the tissue prior to dissecting the same).

In another embodiment of the visualization stylet 7, a larger camera can be used that can be accommodated by a larger diameter Veress needle than the one described in TABLE 1. In this case for example, Omnivision CMOS sensor OV06930 with 1.87 mm square cross sectional profile could be used. An appropriately larger micro objective 28 needs to also be used with such sensor, compared to the one earlier disclosed for the smaller stylet construct. Such larger sensor would result in a construct of identical functionality as the one described earlier but with larger dimensions (for both modified Veress needle 12 and visualization stylet 7) as outlined in the table below:

TABLE 2

Critical dimensions of a larger embodiment of the proposed device. The table headers are explained in FIG. 4A.

| $V_{od}$ | $G_{id}$ | $S_{od}$ | $SS_{od}$ |
|---|---|---|---|
| 3.1 mm | 2.8 mm | 2.7 mm | 1.7 mm |

Even if a larger digital camera is used (than the one proposed in TABLE 1), it is preferred that the size of the needle, 17 $V_{od}$, remains small enough that it requires a minimal size incision for it to be pushed through the abdomen. This way even a slightly larger visualization stylet construct 7 (than the one proposed in Table 1) can be conducive to simple, outpatient, microlaparoscopies with possibly little or no anesthesia, while providing the physician with adequate image quality (greater than 50,000 pixels). For this larger embodiment it is preferred that 17 $V_{od}$ does not exceed 3.1 mm.

In another modality of use, the user can utilize a standard completely unmodified Veress needle 1 (FIG. 1A) for the initial puncture and insufflation. Then remove this unmodified 1 needle, and insert the modified needle 12 (FIG. 1B)

and subsequently use the visualization stylet 7 for further diagnosis of the insufflated abdomen. Or similarly, after the initial puncture is made with an unmodified Veress needle 1 and pneumoperitoneum is achieved, the user unscrews the middle spring-loaded insert 2 (gas-flowing tube) from the inserted Veress needle 1 leaving only the needle sheath 4 in place through the abdomen. Then quickly connect a custom Y-hub 20 (whose proximal end 41 is outfitted with a thread that mates with the female threads of the proximal end 49 of the outer needle sheath) onto the proximal end of the needle shaft and then insert the visualization stylet through it. From here on the use of the device can proceed as described earlier. In this modality, no modifications at all are necessary to be made to the Veress needle 1, but the initial insertion of the needle is done blindly; the visualization stylet is inserted immediately after insufflation is completed.

Figure 6A:
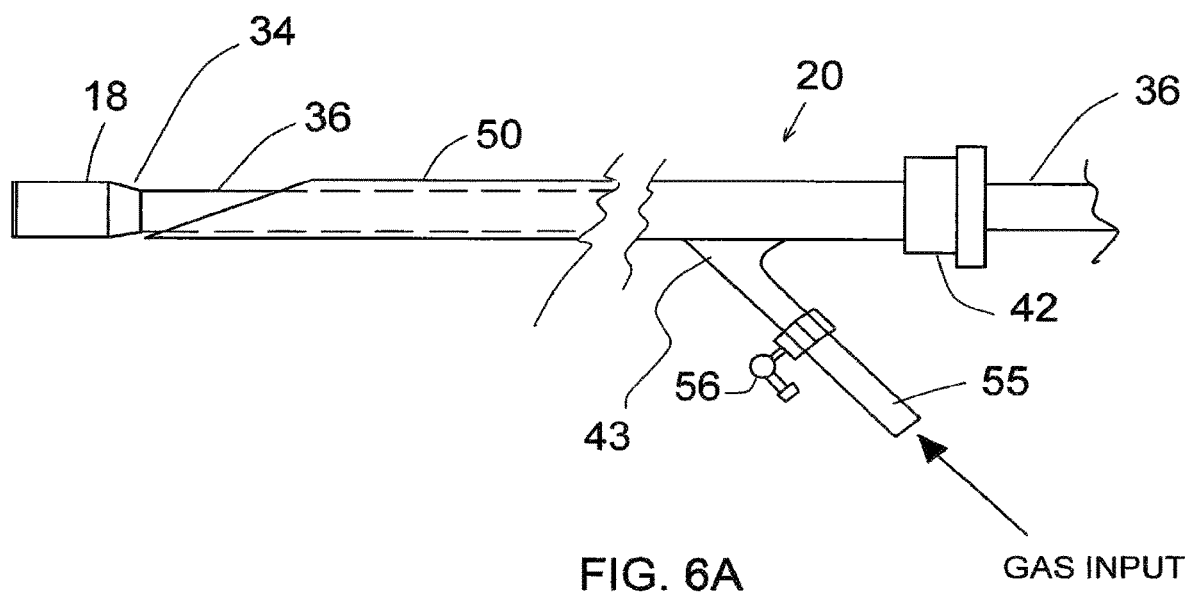
FIG. 6A is a side view showing another embodiment of the invention, with the visualization stylet inserted through a different type of needle.

FIG. 6A shows a variation of the invention in which a needle 50, which can be about the same OD 17 as a Veress needle (1 or 12), and in any event no greater than about 2.2 mm outer diameter (preferably 2.0 mm or smaller), receives the visualization stylet 52 of the invention, without the presence of any gas flow tube (2 or 10) such as included in the modified Veress needle 12 described above. This can enable the OD (and ID) of the needle 50 to be smaller than the Veress needle described above to accommodate a visualization stylet 52 of the same size as described above, or it can enable the visualization stylet 52 to be larger, since the inner, slidable gas tube 10 is not included. Again, the clearance between the narrower, elongated stiff segment 36 of the visualization stylet 52 within the inner cannula 10 of the insertion needle 50 is sufficient to allow a gas flow around the stylet (when the enlarged distal tip 18 is extended as shown) of at least 15 L/min., or more preferably at least 35 L/min. through this annular space without activating any pressure alarms. In a preferred embodiment this is represented by a clearance area slightly greater than 1.7 sq. mm, as in the first embodiment. From TABLE 1 (which describes the Veress needle shaft 4 and stylet 7), $(\pi/4)*(1.7^2-0.8^2)$ =1.767=². In any event, the minimum clearance area for gas flow in either embodiment is about 1 sq. mm, or more preferably about 1.5 sq. mm. This is more easily achieved with the assembly shown in FIG. 6A, but the needle OD can be smaller (or the camera larger) if desired, producing the desired clearance for gas flow, with the FIG. 6A assembly.

As in the conventional Veress needle, gas is emitted from an insufflation gas input 55, controlled by a valve 56, and gas is prevented from backflow by a screw-in hemostatic valve 42. This is shown as part of a Y-hub 20 as in FIG. 2, but it could be a new design, integral with or secured by a fitting (not shown) to the needle 50.

Figure 7:
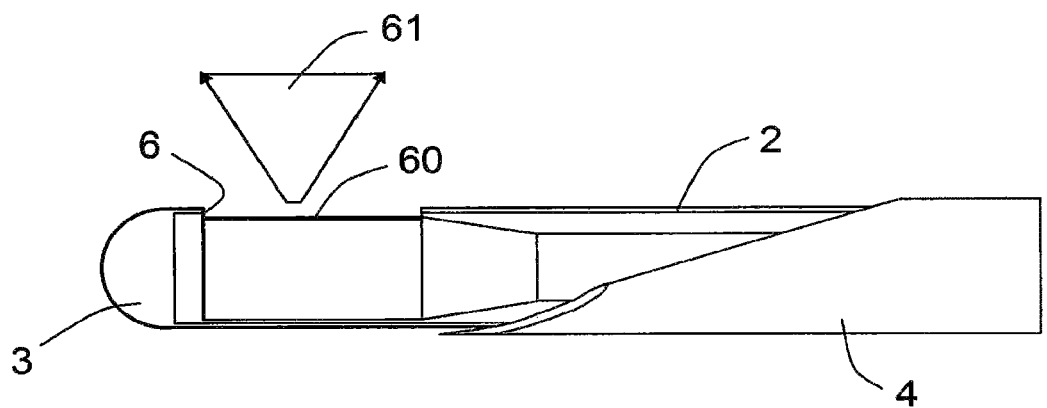
FIG. 7 is a side view of another embodiment, depicting a visualization stylet and modality of use with an unmodified Veress needle, and indicating a side viewing videoscope tip of the stylet.

In yet another embodiment indicated in FIG. 7, the visualization stylet could be constructed with 90-degree side-viewing optics and illumination. Those knowledgeable in the art of endoscopy understand how to construct such videoscope. In this case a completely unmodified Veress needle 1 could be used, FIG. 1A. In this embodiment, the distal side-viewing tip 60 of the stylet will be moved to line up with the side-window 6 of the gas-flowing sheath 2 of the unmodified Veress needle 1, (FIG. 7). Side port holes (not shown in FIG. 7) may be drilled on the side of the gas-flowing sheath 2 proximal to the side-window 6. This way gas may flow while the side-viewing stylet is inserted in the gas-flowing tube 2. The disadvantage of this embodiment is that the stylet will only be able to perform distal viewing at 90 degrees to the central axis of the shaft of the Veress needle, from within the needle only. The side viewing direction of the stylet is indicated by arrows 61.

Figure 8:
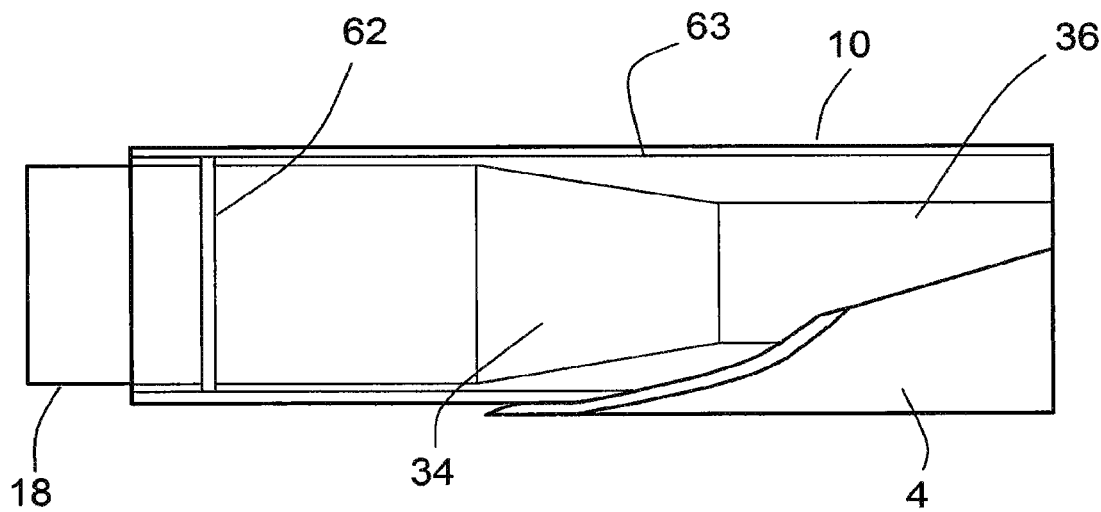
FIG. 8 is a detail view, partially in section, showing the distal tip of the visualization stylet of the first embodiment, with an O-ring for clearing of debris.

In another embodiment, the enlarged diameter tip 18 of the visualization stylet 7 may be adapted to have a rubber o-ring 62 protruding around the circumference of the tip 18 to allow for clearing of debris from the Veress needle 12 as visualization stylet is moved up and down the axis of the penetrating Veress needle, FIG. 8. In this case Equation 1 is violated, but the O-ring 62 is compliant. The O-ring can protrude just enough to make contact with the gas-flowing sheath ID 63 but yet allow for the visualization stylet to be pushed back and forth inside it.

In yet another embodiment, the stylet handle 31 can be made so that it is not permanently attached onto the shaft 15 of the visualization stylet 7 during its final assembly, like in FIG. 2. Instead, a mechanical friction mechanism that can be locked and unlocked by the surgeon during use can allow the handle to rotate freely around the shaft 15 of the visualization stylet. The surgeon then can lock the handle onto the shaft when he observes some preferred orientation of the pointing of the camera with respect to the orientation of the handle dial.

Figure 9:
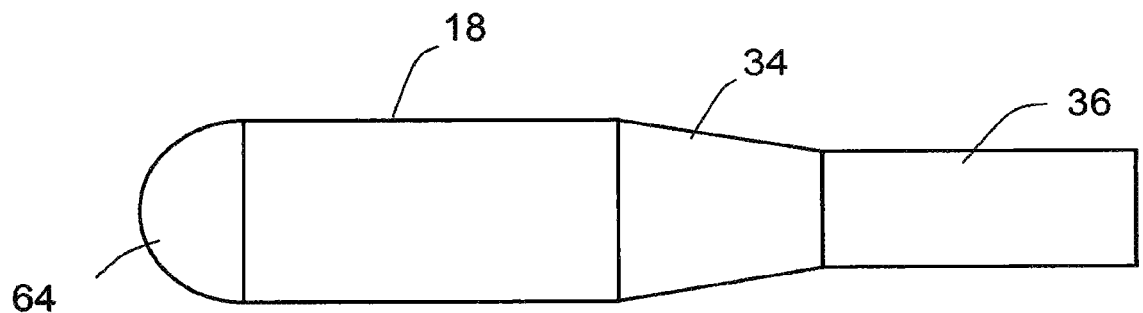
FIG. 9 is a side view showing a visualization stylet with a transparent dome as the distal end.

In another embodiment, the distal end of the stylet can have a protective transparent rounded cover 64 made out of glass or polymer. It should be optically clear so that both the illumination light can get through it as well as images of the area distal to the tip can be taken by the digital image sensor. Such cover 64 can offer a protection from contaminants getting onto the distal flat polished optical surface of the lens and illumination fibers, as well as introduce a blunter surface for the distal end of the visualization stylet, FIG. 9.

Figure 10A:
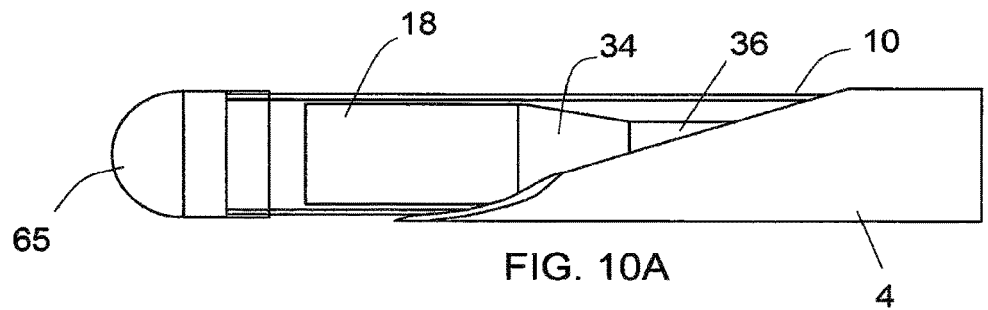
FIGS. 10A and 10B show an embodiment of a Veress needle with a bioabsorbable cap on its gas-flowing sheath.
Figure 10B:
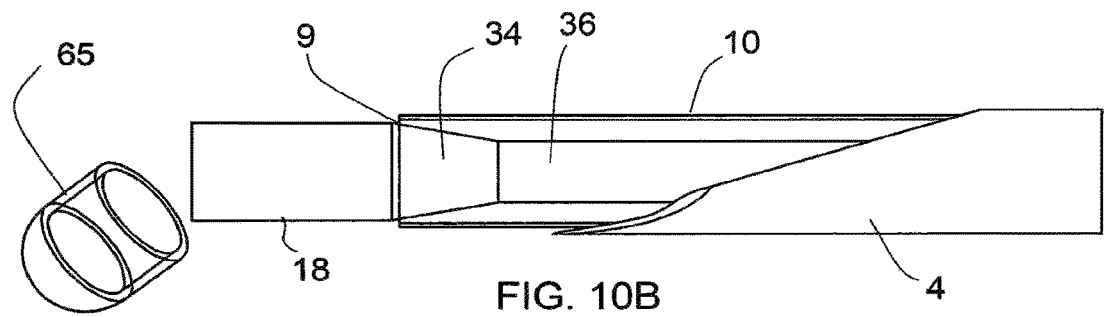

In yet another embodiment, the modified gas-flowing sheath 10 of FIG. 1B of the modified Veress needle 12 can be outfitted to have a protective rounded cap 65, FIG. 10A. This way when the Veress needle first punctures into the abdominal cavity the rounded soft tip 65 would be the part that could come in contact with any of the organs (before insufflation) since it is attached to the spring-loaded inner cannula 10 of the modified Veress needle 12. Thus the soft protective rounded tip 65 of this embodiment can act as the blunt tip of the unmodified Veress needle 1 of FIG. 1A, and serve the same function. This protective cover 65 is preferred to be made out of a bioabsorbable material. The cover 65 can be moved out of the way by being pushed out with some insert that can fit through the gas-flow sheath 10 of the modified Veress needle 12 (including the distal tip 18 of the visualization stylet 7), FIG. 10B. The cover 65 can fall into the abdominal cavity, the distal tip 18 of the stylet can get pushed distal to the gas-flow sheath, insufflation can commence, and since the cover is bioabsorbable the surgeon does not need to look for it or remove it from the body.

In another embodiment of the stylet, the handle 31 has an optical port 66 (FIG. 11): Instead of the illumination fibers 19 continuing intact from distal tip all the way to the proximal optical connector 22 of the flexible portion 21 of the visualization scope 7 for connection to an external light source (like in FIG. 2), the illumination fibers 19 get terminated at the proximal end of the handle 66, FIG. 11A. A light guide (fiber or liquid) is connected to a light source 24 to transmit the light (completely independently from the visualization stylet), which in this case has only one electrical connector 23, FIG. 11A. A much larger diameter light guide 67 can be connected between light source 24 and optical port 66 on handle 31. Such optical fiber bundle 67 can transmit much more light than the small fibers 19 used for illumination in the visualization stylet. Those knowledgeable in the art of illumination and optics understand how the light source and connector of FIG. 11A can be constructed for optimum coupling into a larger light guide.

Furthermore, standard endoscopic practices show how a light guide can connect onto an optical interface on the proximal end of a scope.

In a different embodiment (FIG. 11B), an LED light source 68 can be directly coupled onto the optical port 66 on the handle 31. Such LED can be battery powered and in this case again the visualization stylet has only one electrical connector.

Finally in yet another embodiment, the handle contains a wireless transmitter/receiver 69 (battery powered) that transmits the electrical signals to the image processing hardware 25 which now needs to include a wireless transmitter/receiver 69. In this case the visualization stylet has no wires coming off its proximal end, FIG. 11C.

Figure 11A:
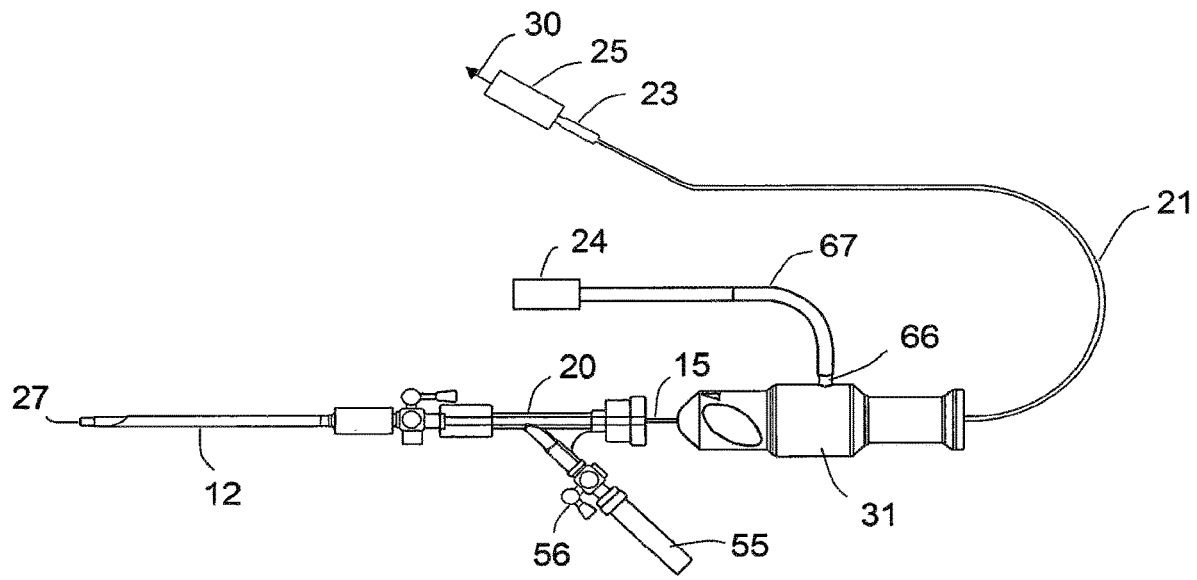
FIG. 11A shows the visualization stylet as inserted through the Veress needle essentially as in FIG. 2, in a modified embodiment wherein the stylet has illumination fibers terminating at an optical interface in the handle of the stylet, with a larger light guide used to transmit light from a light source to the optical interface for delivering light to the distal end.
Figure 11B:
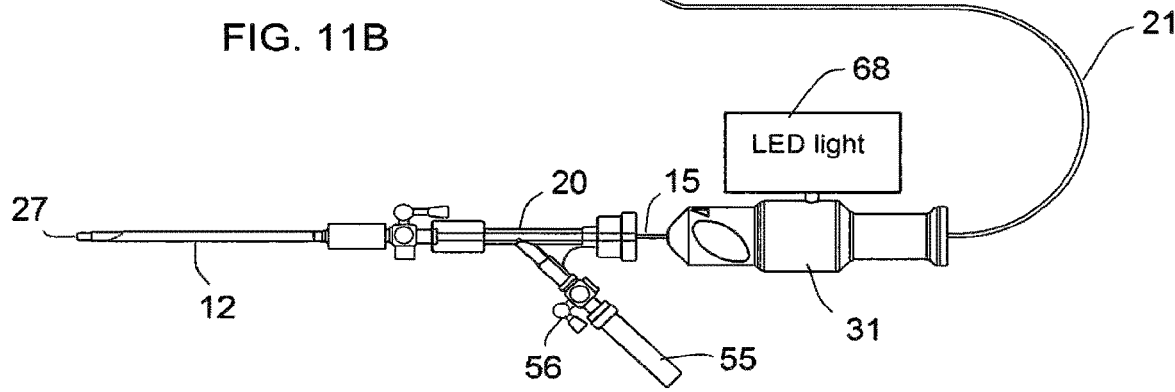
FIG. 11B shows another modified assembly similar to that of FIG. 11A, wherein a light source is directly attached onto the handle of the stylet at the optical interface.
Figure 11C:
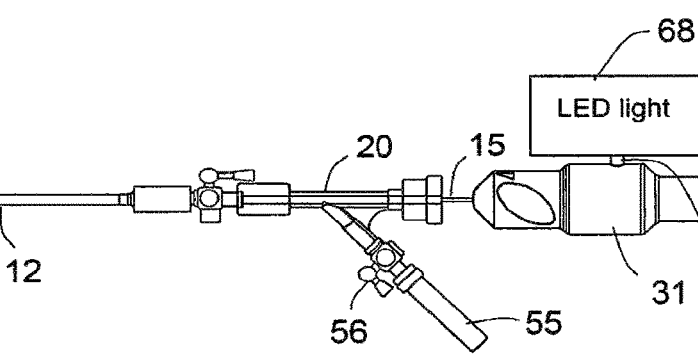
FIG. 11C is also similar to FIG. 11A but shows a visualization stylet with an optical interface on the handle and without an electrical connector. Again illumination fibers terminate at the optical interface, with a light source directly attached onto the handle at the optical interface. Wireless electronics inside the handle transmit signals to an image processing interface and vice versa.

In yet another embodiment, the handle 31 may also contain a switch on its outside surface (not shown in FIG. 11). Such switch can be easily accessible (even blindly) by the surgeon's hand/fingers during the procedure. The switch can be used to initiate the capture of images or live video onto the storage device in the video processing hardware 25. A plurality of knobs and switches can be attached onto the handle to control all aspects of illumination and electronic control of the camera. Any other logical permutations of the embodiments depicted in FIG. 11A-FIG. 11C are also included in this application.

Finally in another embodiment of the system, the light source (24 or 68) used to provide illumination for the visualization stylet (any of the light-source manifestations depicted in FIG. 2 and FIG. 11) can be such that it can accommodate Narrow Band Imaging (NBI). Such light sources are commercially available and those knowledgeable in the art of illumination, optics, and endoscopy should know how to put one together. Such illumination can be used to exploit recently discovered applications of Narrow Band Imaging (NBI). Termed "electronic chromoendoscopy" by some quarters, this unique technology was first described by Gono (Gono K, et. al. *"Appearance of enhanced tissue features in narrow-band endoscopic imaging." J Biomed Opt.* 2004; 9: 568-577). The narrowed bandwidths of green and blue light lead to superficial penetration of the mucosa accentuating the microvasculature pattern, as hemoglobin has a peak absorption spectrum towards both these wavelengths. The quality of the surface pit pattern morphology is also clearly enhanced by this technology. Thus in this embodiment, the proposed miniature visualization stylet can be used as an NBI endoscopic tool during a laparoscopy as well.

It is appreciated that the concept of the invention may be applied to any surgical instrument that provides the ability to insufflate under direct vision of the site of insufflation, regardless of the size of the instrument and the type of insufflation fluid.

The above described preferred embodiments are intended to illustrate the principles of the invention, but not to limit its scope. Other embodiments and variations to these preferred embodiments will be apparent to those skilled in the art and may be made without departing from the spirit and scope of the invention.

We claim:

1. A method for pneumolaparoscopic surgery, comprising:
   providing a hollow needle having an outside diameter no greater than about 2.1 mm and a puncturing tip at a distal end of the needle and having a lumen within the needle,
   providing a visualization stylet of a diameter to fit within the lumen of the needle, the visualization stylet comprising a miniature videoscope and having a digital sensor chip camera for producing real video images of tissue penetrated by the needle and illumination means at a distal end of the visualization stylet, with a connecting cable extending from the camera through an elongated shaft of the visualization stylet to a stylet hub for connection to image processing and display equipment,
   inserting the visualization stylet through a proximal end of the needle so that the distal end of the visualization stylet with the camera is essentially at the distal end of the needle adjacent to the puncturing tip,
   inserting the needle to penetrate through a patient's torso and into tissues of the torso while viewing the real video image under illumination showing the tissues and the progress of the needle through the tissues,
   when the needle tip has entered the patient's peritoneal cavity and formed a main port, delivering a gas through the needle, through a clearance between the visualization stylet and the lumen within the needle, to inflate the peritoneal cavity to separate the peritoneum from internal organs,
   observing via the video images the position of the needle tip in relation to the gas-separated tissues,
   following insufflation of the peritoneal cavity, removing the needle from the main port along with the visualization stylet,
   penetrating the patient's torso skin and extending the needle with the visualization stylet into the insufflated peritoneal cavity to form a second port at a second port location spaced away from the main port, and with the needle's distal end within the insufflated peritoneal cavity, viewing real video images to observe the main port from within the inflated cavity at said second port, while inserting a large trocar into the original, main port to assure correct placement of the large trocar,
   withdrawing the needle and inserting a second trocar smaller than the large trocar into said second port,
   performing laparoscopic surgery via the large trocar at the main port and the second trocar at the second port, using laparoscopic surgical instruments,
   at conclusion of the laparoscopic surgery, closing the ports by closing the main, large-trocar port while viewing real video images of the main port closure from inside the cavity using the needle and visualization stylet inserted through the second port, thus visually assuring the main port is reliably closed, and
   then removing the needle and visualization stylet and closing the second port externally.

2. The method of claim 1, further including, while the needle is first inserted and the peritoneal cavity is inflated, selecting positions within the inflated cavity for the second port, and, using light directed through the skin from inside the cavity, marking a position on the skin for the second port.

3. The method of claim 1, wherein a third port is formed with the needle, and further including, at conclusion of the laparoscopic surgery, first closing one port of the second and third ports while viewing the closing of the one port from inside the cavity using a scope inserted through the main port, then closing the main port while viewing the main port from inside the cavity using the needle and scope inserted through the other of the second and third ports.

4. The method of claim 1, wherein said elongated shaft of the visualization stylet has a significantly smaller outside diameter than the lumen within the needle, throughout the length of the stylet shaft except at said distal end of the stylet, wherein the stylet shaft is of a larger diameter substantially filling the lumen, and the method including the step of extending the visualization stylet's distal end out of the needle to an extent that gas can pass freely out the distal end of the needle after the needle tip has entered the patient's peritoneal cavity.

* * * * *